United States Patent
Wang et al.

(10) Patent No.: US 12,217,384 B2
(45) Date of Patent: Feb. 4, 2025

(54) CONTRAST ENHANCEMENT METHOD FOR THE OBJECTS WITH INTRINSIC PARTIAL VOLUME EFFECT

(71) Applicants: University of Cincinnati, Cincinnati, OH (US); Children's Hospital Medical Center, Cincinnati, OH (US)

(72) Inventors: Jinghua Wang, Mason, OH (US); Lili He, Mason, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 390 days.

(21) Appl. No.: 17/795,279

(22) PCT Filed: Jan. 26, 2021

(86) PCT No.: PCT/US2021/014986
§ 371 (c)(1),
(2) Date: Jul. 26, 2022

(87) PCT Pub. No.: WO2021/154671
PCT Pub. Date: Aug. 5, 2021

(65) Prior Publication Data
US 2023/0072303 A1    Mar. 9, 2023

Related U.S. Application Data

(60) Provisional application No. 62/967,207, filed on Jan. 29, 2020.

(51) Int. Cl.
*G06T 7/11*    (2017.01)
*G06T 3/40*    (2006.01)
(Continued)

(52) U.S. Cl.
CPC .............. *G06T 3/40* (2013.01); *G06T 5/94* (2024.01); *G06T 7/0012* (2013.01); *A61B 6/481* (2013.01);
(Continued)

(58) Field of Classification Search
CPC ........... G06K 9/00261; G06K 9/00288; G06K 9/00228; G06K 9/00268; G06K 9/00281;
(Continued)

(56) References Cited

U.S. PATENT DOCUMENTS 5,768,413 A    6/1998  Levin et al.
6,633,684 B1   10/2003 James
(Continued)

FOREIGN PATENT DOCUMENTS

| WO | 2019002560 A1 | 1/2019 | |
|---|---|---|---|
| WO | WO-2019157119 A1 * | 8/2019 | ........... A61B 5/0042 |
| WO | 2020072784 A9 | 4/2020 | |

OTHER PUBLICATIONS

International Search Report and Written Opinion mailed Apr. 21, 2021 in reference to co-pending Application No. PCT/US2021/14986 filed Jan. 29, 2020.

*Primary Examiner* — Quan M Hua
(74) *Attorney, Agent, or Firm* — Dinsmore & Shohl LLP

(57) ABSTRACT

A method for spatial resolution enhanced imaging is provided. The method includes determining a target region of a subject being imaged; estimating an achievable spatial resolution; selecting an increased spatial resolution that is greater than a predetermined spatial resolution and equal to or less than the achievable spatial resolution; and acquiring image data of the target region with the increased spatial resolution. A method for enhancing the contrast between the region of interest and other tissue region in the image data acquired with the increased spatial resolution and other (Continued)

tissue region in image data acquired with the predetermined spatial resolution due to the intrinsic partial volume effect is also provided.

20 Claims, 8 Drawing Sheets

(51) Int. Cl.
*G06T 5/94* (2024.01)
*G06T 7/00* (2017.01)
*A61B 6/00* (2006.01)
*A61B 8/08* (2006.01)

(52) U.S. Cl.
CPC ..... *A61B 8/481* (2013.01); *G06T 2207/10088* (2013.01); *G06T 2207/30096* (2013.01)

(58) Field of Classification Search
CPC ......... G06K 9/6202; G06K 2009/4666; G06K 9/00362; G06K 9/4642; G06K 9/6206; G06K 9/6255; G06K 9/6256; G06K 9/00275; G06K 9/00308; G06K 9/00926; G06K 9/3233; G06K 9/4671; G06K 9/6215; G06K 9/6228; G06K 9/6262; G06K 9/627; G06K 9/6276; G06K 9/629; G06N 3/0454; G06N 3/084; G06N 3/08; G06T 11/00; G06T 2207/10016; G06T 2207/10024; G06T 2207/20081; G06T 2207/30201; G06T 2207/30241; G06T 2207/30244; G06T 7/251; G06T 7/74; G06T 7/80

See application file for complete search history.

(56) References Cited

U.S. PATENT DOCUMENTS

| | | | |
|---|---|---|---|
| 6,757,442 | B1 | 6/2004 | Avinash |
| 7,727,155 | B2 | 6/2010 | de Ziegler |
| 8,378,134 | B2 | 2/2013 | Grimmond et al. |
| 8,774,480 | B2 | 7/2014 | Roy et al. |
| 9,372,245 | B2 | 6/2016 | Singh et al. |
| 10,055,827 | B2 | 8/2018 | Zhou et al. |
| 10,407,412 | B2 | 9/2019 | Boi et al. |
| 10,525,152 | B2 | 1/2020 | Sigalov |
| 2004/0004188 | A1 | 1/2004 | Tai |
| 2016/0093023 | A1* | 3/2016 | Prasad ................. G06F 3/0486 382/173 |
| 2017/0053414 | A1* | 2/2017 | Flohr ....................... A61B 6/12 |
| 2018/0280544 | A1 | 10/2018 | Yang et al. |
| 2019/0026873 | A1 | 1/2019 | Luciano et al. |
| 2019/0056470 | A1 | 2/2019 | Wang |
| 2019/0231288 | A1* | 8/2019 | Profio .................... A61B 6/484 |

* cited by examiner

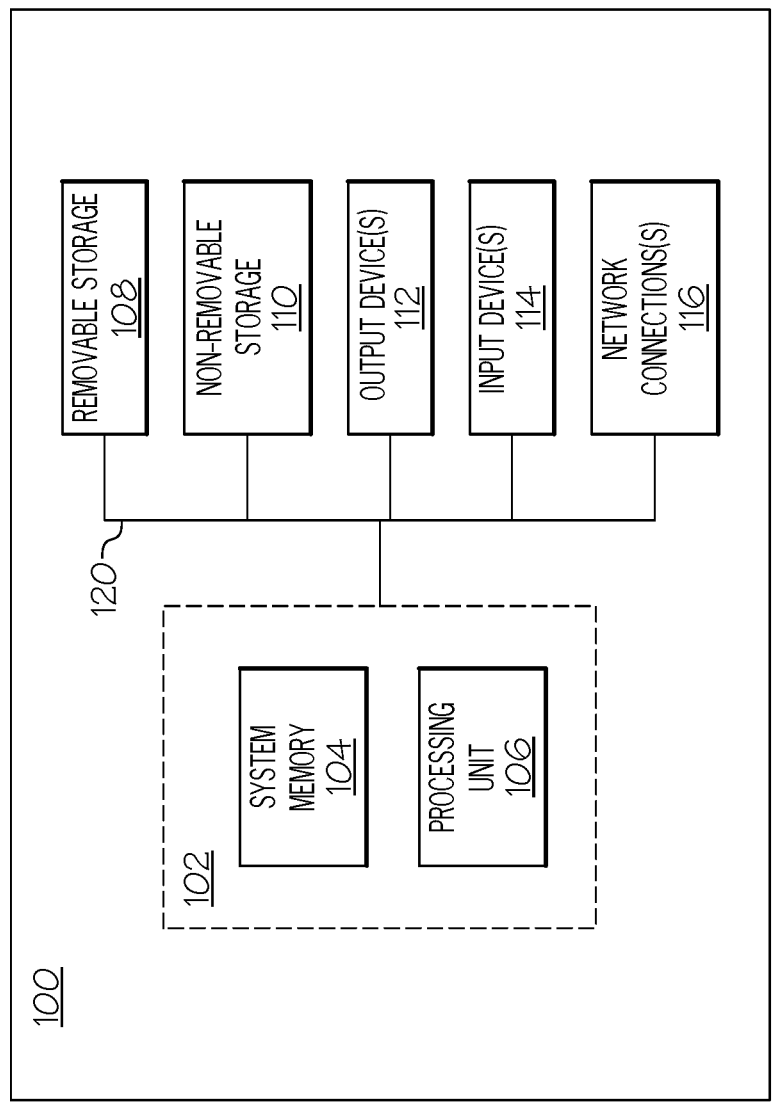

CONTRAST ENHANCEMENT METHOD FOR THE OBJECTS WITH INTRINSIC PARTIAL VOLUME EFFECT

CROSS-REFERENCE TO RELATED APPLICATIONS

This application is a National Stage Entry under 35 U.S.C. § 371 of International Patent Application No. PCT/US2021/014986, filed Jan. 26, 2021, which claims priority to the benefit of the filing date of U.S. Provisional Application No. 62/967,207, entitled "Spatial resolution enhanced cancer imaging" filed on Jan. 29, 2020, which is hereby incorporated by reference in its entirety.

BACKGROUND

1. Field of the Invention

The present invention relates to systems and methods for contrast enhancement in objects including a region of interest with intrinsic partial volume effect by increasing spatial resolution for imaging.

2. Description of the Related Art

Sufficient signal intensity in acquired images of patients are important for medical practices. Medical image enhancement is the process of increasing image quality using image acquisition, image post-processing, and certain substances (called for contrast agents). Major medical imaging acquisition techniques include, but not limited to, X-ray, computed tomography (CT), ultrasound, magnetic resonance imaging (MRI), magnetic resonance spectroscopy (MRS), magnetic resonance spectroscopy imaging (MRSI), positron emission tomography (PET), near-infrared (NIR) fluorescence imaging, nuclear medicine imaging, and their variations. Different imaging techniques generate a medical image of internal structure and tissue. Various image post-processing methods have been proposed to improve the signal intensity in medical practices. These methods include edge sharpening, smoothing, blurring, histogram equalization, gamma correction, dithering, color palate selection, paint brush effects and texture rendering, wavelet-based enhancement, histogram equalization, 2D empirical mode decomposition, decorrelation stretching methods, PDE-based, stochastic resonance, Gamma correction, and median filter-based methods. But the major limitation of these methods is to lose some image information and cause artifacts. Additionally, these methods also are limited by their performance that generally improves image quality by less than 20%.

Contrast enhancement is a particular aspect of image enhancement. Most techniques used for image enhancement can also applied for contrast enhancement, including image post-processing, and contrast agent techniques. For example, a number of post-processing-based techniques are disclosed in the following references:

U.S. Pat. Nos. 6,633,684 and 6,677,959 to James describe a contrast enhancement method by fitting an original image and expanding the dynamic color range. Such expansion may visually amplify subtle structures, thereby generate a contrast-enhanced image.

U.S. Pat. No. 6,757,442B1 to Gopal B. Avinash discloses a contrast enhancement method. His method separates structural regions from non-structural regions, and respectively smooth and sharpen functions on the separated regions. Non-uniform equalization is used to reduce differences between high and low intensity values, and then perform contrast enhancement by the equalized values.

U.S. Pat. No. 8,228,560 to David Sheldon Hooper discloses a method for contrast enhancement of digital images using one or more filtered images to generate offsets and multipliers for adjusting pixel color values, thereby generating a contrast-enhanced image from the original image.

U.S. Pat. No. 8,774,480B2 to Prasun Roy and Subramanyam Rallabandi discloses a novel medical image enhancement based on the Integral Transform of the image.

U.S. patent Ser. No. 10/055,827B2 to Chunhong Zhou et al. discloses a method for image contrast enhancement. Their method performs contrast enhancement method through multiplication of the invariant factor, leading to a certain brightness level invariant before and after the enhancement process.

U.S. Patent Application Publication No. 20190026873 to Vincent Luciano and Fred Wood discloses an apparatus and method for the contrast enhancement of vein pattern to avoid improper patient care or injury.

Moreover, contrast agents are often used to increase signal intensity and contrast between tissues in medical imaging acquisition. For example, gadolinium (Gd)-based MRI contrast agents may make certain tissues, abnormalities, or diseases more clearly visible when it is administered by injection or orally in MRI examinations. The contrast agent expands the range of signal intensities detected during the examination and permits the detection of a wide variety of pathologic processes, including inflammation, infection, and malignancy, that would otherwise be undetectable with unenhanced MR imaging or other imaging modalities, for example, brain metastases. Although many imaging modalities can be performed without the injection of contrast agents, contrast agents enhance the visualization of internal tissues and organs, leading to better applications of medical imaging in diagnoses and treatment assessments. A number of contrast agents have been developed for contrast enhancement in medical imaging. However, the wide application of the contrast agents is limited sometimes. For example, gadolinium (Gd)-based MRI contrast agents could be applied for patients with renal or hepatic dysfunction. Various contrast agent-based techniques for contrast enhancement are disclosed in the following references:

U.S. Pat. No. 7,727,155B2 to Dominique de Ziegler discloses a contrast agent for contrast agent enhancement during ultrasound, MRI, x-ray, PET CT scans, and similar procedures.

U.S. Pat. No. 8,378,134 to Brian James Grimmond et al. discloses a contrast enhancement agent comprising a paramagnetic iron chelate to enhance MRI images.

U.S. patent Ser. No. 10/525,152B2 to Alexander B. Sigalov discloses apolipoproteins A-I and/or A-II or fragments are used as structural and targeting agents.

U.S. Patent Application Publication No. 20180280544A1 to Jenny Jie Yang et al. discloses protein contrast agents and targeted protein contrast agents as a magnetic resonance imaging contrast agent.

U.S. Patent Application Publication No. 20190056470 to Jinghua Wang discloses a method for detecting lesion tissue using an optimal contrast agent MRI protocol.

U.S. patent Ser. No. 10/407,412B2 to Valeria Boi et al. discloses a new class of contrast agents which is comprised of chelated complexes with metal ions, particularly suitable for MRI scanning.

U.S. Pat. No. 9,372,245B2 to Anup Singh et al. discloses a method for Chemical Exchange Saturation Transfer (CEST) contrast enhancement effect by the frequency-selective saturation RF pulses.

U.S. Patent Application Publication No. 20190231288 to Mark Vincent Profio et al. discloses a method and system for contrast-enhanced CT diagnostic imaging. The method comprises estimating a scan time, response time, and time to peak for monitoring the contrast flow, and thereby reducing radiation dose and improving image quality.

International Publication No. WO2019/002560 to Pierre Hoornaert et al. discloses a device for X-ray image contrast enhancement of a vascular structure.

International Publication No. WO2019/157119 to Jinghua Wang and Lili He discloses a method for detecting blood-tissue barrier breakdown or disruption using contrast enhanced MRI after administrating exogenous or endogenous tracers.

International Publication No. WO2020/072784 to Darren Woodside et al. discloses chelators or dies attached to a targeting agent for use in medical imaging.

Since there exist some limitations of both post-processing-based and contrast agent-based techniques for medical image contrast enhancement, there is a critical need in the art to overcome the limitations of these existing techniques.

SUMMARY

The present invention now provides a process to enhance the contrast of the objects including regions of interest with intrinsic partial volume effect by increasing spatial resolution. The proposed apparatus and method provide unique advantages over post-processing methods and contrast agent enhanced methods. Additionally, the present invention may be extended to any medical imaging modalities, including CT, X-ray, MRI, PET, and ultrasound imaging ultrasound, etc.

The present disclosure describes methods and systems for spatial resolution enhanced medical imaging for the objects including a region of interest with intrinsic partial volume effect herein. It should be understood that the present disclosure contemplates magnetic resonance imaging with Gd-based contrast agent, which are provided as an example only, with the techniques described herein. As a result, the present disclosure provides spatial resolution enhanced medical imaging which will provide various medical imaging for all research, drug development, and clinical practices. Additionally, the present methods and apparatuses could be available for any medical imaging modalities with and/or without the contrast agents, including X-ray, computed tomography (CT), ultrasound, but not limited to, magnetic resonance imaging (MRI), magnetic resonance spectroscopy (MRS), magnetic resonance spectroscopy imaging (MRSI), positron emission tomography (PET), near-infrared (NIR) fluorescence imaging, nuclear medicine imaging, and their variations.

An example method for spatial resolution enhanced medical imaging is described herein. The example method includes determining a target region of a subject being imaged, estimating an achievable spatial resolution, selecting an increased spatial resolution that is greater than a predetermined spatial resolution and equal to or less than the achievable spatial resolution, and acquiring image data of the target region with the increased spatial resolution. A voxel or a pixel of the image data corresponding to a region of interest in the target region includes intrinsic partial volume effect and another voxel or pixel of the image data corresponding to a boundary of the region of interest in the target region includes extrinsic partial volume effect. A contrast between the region of interest and other tissue region in the image data acquired with the increased spatial resolution is greater than a contrast between the region of interest and other tissue region in image data acquired with the predetermined spatial resolution due to the intrinsic partial volume effect.

An example system for spatial resolution enhanced cancer imaging is described herein. The example system includes a processor configured to: determine a target region of a subject being imaged; estimate an achievable spatial resolution; and select an increased spatial resolution that is greater than a predetermined spatial resolution and equal to or less than the achievable spatial resolution; and a receiver configured to acquire image data of the target region with the increased spatial resolution. A voxel or a pixel of the image data corresponding to a region of interest in the target region includes intrinsic partial volume effect and another voxel or pixel of the image data corresponding to a boundary of the region of interest in the target region includes extrinsic partial volume effect. A contrast between the region of interest and other tissue region in the image data acquired with the increased spatial resolution is greater than a contrast between the region of interest and other tissue region in image data acquired with the predetermined spatial resolution due to the intrinsic partial volume effect.

The image data of patient may be received from one of, X-ray, computed tomography (CT), ultrasound, but not limited to, magnetic resonance imaging (MRI), magnetic resonance spectroscopy (MRS), magnetic resonance spectroscopy imaging (MRSI), positron emission tomography (PET), near-infrared (NIR) fluorescence imaging, and nuclear medicine imaging.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1A is an example computing device.

DETAILED DESCRIPTION

1. Definition

Figure 1:
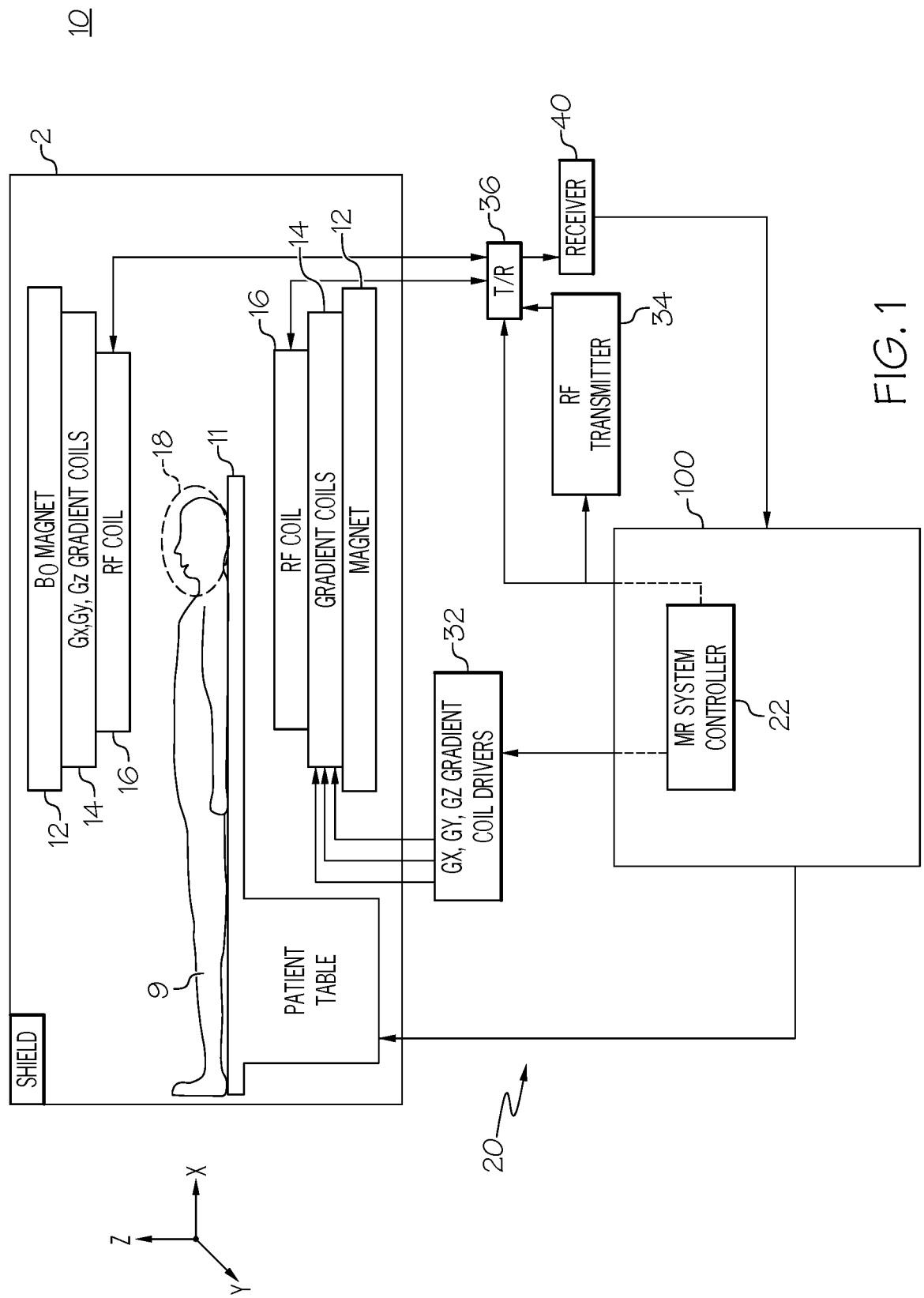
FIG. 1 is a diagram illustrating an example MRI system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not.

The term "spatial resolution" or "image resolution" and its variations herein is defined as the number of pixels or voxels per length or volume. That is, the spatial resolution is a reciprocal of the pixel or voxel size. The unit of the spatial resolution is per millimeter (mm) or $mm^{-1}$. Higher resolutions mean that there are more pixels or voxels per unit, resulting in more pixel or voxel information in a fixed region of interest. For example, the spatial resolution of MR images is determined by the ratio of the size of image sampling matrix to the size of the field-of-view.

The term "achievable spatial resolution" and its variation herein indicate a maximal spatial resolution which can be reached by medical imaging acquisition with acceptable contrast-to-noise ratio and image acquisition. The various characterizations of an object being imaged strongly influence the achievable spatial resolutions. For example, diffusion, T2 relaxation, and susceptibility of the object being imaged theoretically impact the spatial resolution of MRI acquisition. Additionally, MRI hardware (static magnetic strength, gradient strength, radiofrequency coil sensitivity), image processing and reconstruction algorithms also have a significant influence on the achievable spatial resolution. Finally, imaging parameters such as coverage, a field of view, echo time, etc. and sequences also influence the achievable spatial resolution. The achievable spatial resolution is greater than spatial resolution used in clinical practices, and the achievable spatial resolution generally is not used in clinical practices because higher resolution will lead to the increased cost of scan time. The achievable spatial resolution of a structural human brain image can be 1.5 or 2 per mm at 3.0 T MRI. In contrast, the spatial resolution used in clinical practice is generally less than 1 per mm at 3.0 T MRI. As for PET, the achievable spatial resolution is around 0.5 per mm and the clinical spatial resolution used in clinical practice is around 0.2 per mm.

The term "partial volume effect" and its variation herein are defined as a pixel or a voxel that includes multiple components with different characterizations. Herein partial volume effect is divided into two types here: intrinsic or extrinsic partial volume effect. The extrinsic partial volume effect occurs at the boundary of different tissues or different regions. There is no extrinsic partial volume effect within the tissues or the regions. For example, there exist partial volume effect of brain MRI image at the gray matter-white matter boundary. The intrinsic partial volume effect occurs both within the region of interest and at the boundary of different regions. For example, there exists intrinsic partial volume effect of contrast enhanced MRI tumor images within contrast enhanced tumor regions that includes normal tissue cells and tumor cells with or with contrast agent leakage. The size of the tumor regions can be much larger than that of pixel or voxel of radiological images. According to the present invention, the increased spatial resolution can increase the contrast for radiological images including the intrinsic partial volume effect when the size of regions of interest is comparable to the size of a pixel or a voxel of radiological images. The intrinsic partial volume effect widely exists in biomedical imaging. For example, many lesions defined as radiological images, such as tumor, include different cells or molecules or gene types which are differentiated by image radiomic features. Additionally, physiological regions defined as radiological images includes the same cells or molecules with different physiological property. For example, there are both active and non-active neurons in visual cortex that can be differentiated by high-resolution functional MRI.

The terms "image enhancement" and their variation herein indicate a process that improves image quality, including at least one of reducing noise, increasing signal intensity, increasing sharpness, enhancing image contrast, and enhancing edge of tissues. Common practices include image post-processing, application of contrast agents, and optimization of image modalities and protocols.

The terms "contrast enhancement" and their variation herein indicate a particular aspect of image enhancement. Most techniques used for image enhancements could be used to perform the contrast enhancement. For example, a simple contrast stretch is used to increase dynamic range of image intensity and enhance the contrast of a displayed image by post-processing.

The terms "contrast agent" or "contrast medium" and their variation herein indicate a substance used to increase the contrast or improve more information of structures or fluids within the body in medical imaging so that the radiologists enable to distinguish normal from abnormal conditions. The contrast agent may be used to diagnose disease as well as monitor treatment effects. The contrast agent includes exogenous contrast agents and endogenous contrast agents. The exogenous contrast agents may be administered by oral or intravenous administration. For example, MRI contrast agents are used to improve the visibility of internal body structures. The most commonly used compounds for contrast enhancement are gadolinium-based compounds which shorten the relaxation times following oral or intravenous administration. The disadvantage of exogenous tracers is that there are side effects associated with the administration of the tracers. For example, the injection of exogenous agent of Gd-based contrast agent in MRI has potential side effects of nephrogenic systemic fibrosis (NSF), deposition of Gd molecules, and potential neurotoxicity. The endogenous contrast agents depend on the intrinsic ability to increase the contrast or improve more information of structures or fluids within the body in medical imaging. For example, arterial spin labelling MRI uses magnetically labeled arterial blood water protons as an endogenous contrast agent to measure tissue perfusion. The endogenous contrast agent method has a very promising clinical screening and management because the injection of exogenous contrast agent has potential risk for patients.

The terms "heterogenous objects" or "heterogenous regions of interest" and their variation herein indicate objects including at least one region of interest with intrinsic partial volume effect. The word heterogeneous is used as an opposition to "homogenous objects" or "homogenous regions of interest". For example, cancer cells with and without blood brain disruption, and normal brain tissue cells in a voxel, or pixel and brain cancer lesions always mix together to contribute signal intensity of the cancer lesions in brain cancer imaging.

The terms "homogenous objects" and their variation herein indicate the objects only including region of interest with extrinsic partial volume effect. The terms "therapy" and "treatment" as used interchangeably herein, refer to an intervention performed with the intention of improving a subject's status.

The terms "pathological and physiological features" and their variation herein indicate features determined by medical images which are associated with pathology and physiology. Pathology describes conditions observed during a disease state, whereas physiology describes processes or mechanisms operating within an organism.

The terms "detection" and "diagnosis" as used interchangeably herein, refer to identify the abnormal tissue or lesion.

As used herein, image contrast is defined as:

$$\text{Contrast} = 2 * \frac{\mu_A - \mu_B}{\mu_A + \mu_B}, \quad \text{Equation (1)}$$

where $\mu_A$ and $\mu_B$ are the average signal value of regions A and B, respectively. The image contrast is invariant as a function of voxel size or spatial resolution.

Example Imaging System

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Example Computing Device

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1.

Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Spatial Resolution Enhanced Medical Imaging

The key metrics for evaluating image quality include the signal intensity and contrast of a target regions of interest. The high signal intensity does not guarantee a good image quality in clinical practices. In clinical practices, the images are expected to distinguish lesions from neighboring normal tissue. The detection and visibility of lesions in medical imaging strongly depends on lesion-tissue CNR. Generally, the signal intensity of medical imaging decreases with the increasing spatial resolution. For example, the signal intensity of MR images is proportional to the quantity of spins or voxel size. The contrast is invariant as a function of a spatial resolution or a voxel size when a voxel or pixel signal comes from a homogenous portion of tissue within the voxel or pixel, even when the size of the homogenous portion of tissue is less than that of the voxel or pixel. In the present disclosure, the effect of changing a spatial resolution or a voxel size on the object of interest with intrinsic partial volume effect is described both theoretically and experimentally. The present invention provides a novel method for contrast enhancement of the object of interests with intrinsic partial volume effect by increasing spatial resolutions.

Figure 2:
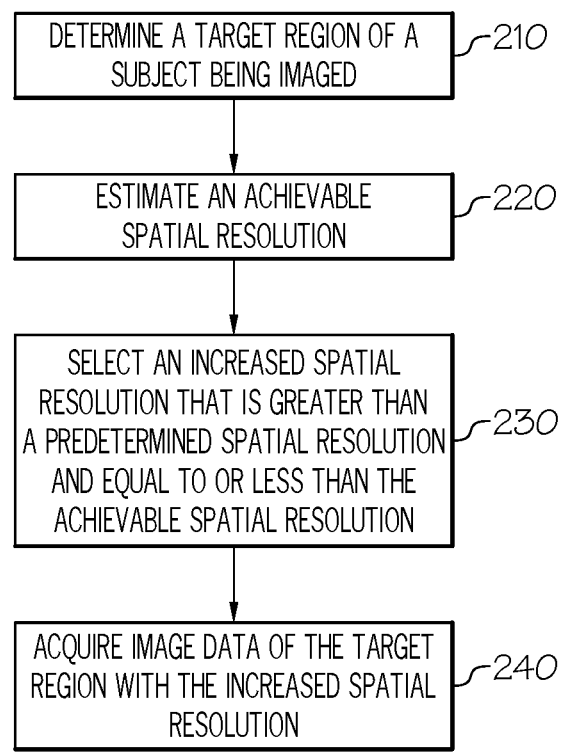
FIG. 2 is a flowchart illustrating example operations for spatial resolution enhanced medical imaging according to one example in the present disclosure.

FIG. 2 is a flowchart illustrating example operations for spatial resolution enhanced medical imaging.

In step 210, an MRI system determines a target region of a subject being imaged. For example, the brain of the subject may be target region of the subject.

In step 220, the MRI system estimates an achievable spatial resolution. The achievable spatial resolution is a maximal spatial resolution which can be reached by medical imaging acquisition with acceptable contrast-to-noise ratio and image acquisition. The achievable spatial resolution may be determined by various factors including imaging modalities, hardware, imaging parameters, acquisition time, image coverage and image reconstruction. The achievable spatial resolution of a structural human brain image can be around 1.6 per mm for whole brain coverage at 3.0 T MRI. In contrast, the spatial resolution used in clinical practice is generally less than 1 per mm at 3.0 T MRI. As for PET, the achievable spatial resolution is around 0.5 per mm and the clinical spatial resolution used in clinical practice is around 0.2 per mm.

In step 230, the MRI system selects an increased spatial resolution that is greater than a predetermined spatial resolution and equal to or less than the achievable spatial resolution. The predetermined spatial resolution may be a conventional spatial resolution used in clinical or research practice. In one example, the increased spatial resolution is greater than a half of the achievable spatial resolution. In another example, the increased spatial resolution is between a half of the achievable spatial resolution and two thirds of the achievable spatial resolution. In another example, the increased spatial resolution is between two thirds of the achievable spatial resolution and the achievable spatial resolution.

In step 240, the MRI system acquires image data of the target region with the increased spatial resolution. The image data of the subject may be received from one of, X-ray, computed tomography (CT), ultrasound, magnetic resonance imaging (MRI), magnetic resonance spectroscopy (MRS), magnetic resonance spectroscopy imaging (MRSI), positron emission tomography (PET), near-infrared (NIR) fluorescence imaging, nuclear medicine imaging, and their variations A voxel or a pixel of the image data corresponding to a region of interest in the target region includes intrinsic partial volume effect. In embodiments, contrast agent is administered to the subject before acquiring the image data, and the intrinsic partial volume effect may include a cell with contrast agent leakage and a cell without contrast agent leakage. As another example, the intrinsic partial volume effect may include a lesion cell and a non-lesion cell. In some embodiments, the image data is acquired with functional imaging, and the intrinsic partial volume effect may include excited neurons and non-excited neurons. Another voxel or pixel of the image data corresponding to a boundary of the region of interest in the target region includes extrinsic partial volume effect. A contrast between the region of interest and other tissue region in the image data acquired with the increased spatial resolution is greater than a contrast between the region of interest and other tissue region in image data acquired with the predetermined spatial resolution due to the intrinsic partial volume effect.

The voxel or pixel of the image data corresponding to the region of interest with intrinsic partial volume effect further includes cells and molecules with the different pathological or physiological features that can be characterized by radiomic features derived from the radiological images.

The heterogenous regions of interest indicate the objects including at least one region of interest with intrinsic partial volume effect. For example, cancer lesion always includes normal cells and cancer cells in the image when image voxel or pixel size is larger than the size of cells. The boundary of heterogenous voxel or pixel or region of interest is not apparent, particularly when the voxel or pixel size or region of interest is much less than the size of cells and molecules. Each voxel or pixel or region of interest includes at least two different cells or molecules. The homogenous regions of interest indicate objects only including region of interest with extrinsic partial volume effect. For example, white matter or gray matter can be respectively regarded as a homogeneous region of interest. The image features indicate that markers or indictors are determined by the acquired medical imaging. These image features strongly relate to the pathological and/or physiological changes.

Increased Contrast with Increased Spatial Resolution for the Objects of Interest with Intrinsic Partial Volume Effect Image contrast for two regions of interest E and N can be also defined as Equation (2).

$$\text{Contrast} = 2 * \frac{S_E - S_N}{S_E + S_N}, \quad \text{Equation (2)}$$

where $S_E$ and $S_N$ are the average signal value of regions E and N, respectively. The regions E is assumed to be a region including intrinsic partial volume effect. If a lesion voxel i with the voxel size of $\Delta V$ includes lesion cells E and normal tissue cells N, the combined signal from the lesion voxel is the summed fractional signals of $S_E(i)$ and $S_N(i)$. The contrast between the lesion voxel i and the normal tissue voxel j is given by:

$$\text{contrast}_{\Delta V} = [\alpha(i)S_E(i) + (1-\alpha(i))S_N(i)] - S_N(j) \quad \text{Equation (3)}$$

where $\alpha(i)$ is defined as fraction of lesion cells; $1-\alpha(i)$ is the fraction of normal tissue cells. If it is assumed that the signals from both normal tissue cells and lesion cells are homogeneous; that is $S_N(i)=S_N(j)=S_N$; and $S_E(i)=S_E$, then equation (3) can be simplified to $\text{contrast}_{\Delta V}=\alpha(i)\cdot(S_E-S_N)$. Therefore, lesion-tissue contrast in a multi-voxel lesion region can be given by:

$$\text{contrast}_{\Delta V} = (S_E - S_N)\frac{1}{n}\sum_i^n \alpha(i) \quad \text{Equation (4)}$$

where n is total number of voxels in the tumor region. It is assumes that the $\alpha(i)=\alpha$ is homogenous inside the lesion region, while partial volume effect will lead to the reduced fraction (i.e., $(i)\leq\alpha$) at the lesion-tissue boundary because of the contaminating normal tissue.

$$\text{contrast}_{\Delta V} = (S_E - S_N)\left[\frac{N_{in}}{n}\alpha + \frac{1}{n}\sum_i^{N_b} \alpha(i)\right] \leq \alpha(S_E - S_N) \quad \text{Equation (5)}$$

where $N_{in}$ and $N_b$ are number of voxels inside the lesion region and at the lesion-tissue boundary, respectively. When the voxel size is reduced from $\Delta V$ to $\beta\cdot\Delta V$ ($\beta<1$), total number of voxels in the lesion region will become from n to $\hat{n}/\beta$. The contrast with reduced voxel size can be given by $$\text{contrast}_{\beta\Delta V} = (S_E - S_N)\cdot\beta\cdot\left[\frac{N_{in\beta}}{\hat{n}}\alpha + \frac{1}{\hat{n}}\sum_i^{N_b\beta} \alpha_\beta(i)\right] \quad \text{Equation (6)}$$

where $N_{in\beta}$, $N_{out\beta}$, and $N_{b\beta}$ are the voxel number inside and outside the tumor region as well as at the lesion-tissue boundary after the voxel size is reduced to $\beta\cdot\Delta V$, respectively. $N_{in\beta}+N_{b\beta}+N_{out\beta}=\hat{n}/\beta+N_{out\beta}=n/\beta$. The contrast variation caused by the increasing spatial resolution is calculated using Equations (5) and (6) and given by:

$$\text{contrast}_{\beta\Delta V} - \text{contrast}_{\Delta V} = (S_E - S_N)\cdot \quad \text{Equation (7)}$$

$$\left[\frac{\beta N_{in\beta}}{\hat{n}}\alpha + \frac{N_{in}}{n}\alpha + \frac{\beta}{\hat{n}}\sum_i^{N_b\beta}\alpha_\beta(i) - \frac{1}{n}\sum_i^{N_b}\alpha(i)\right] \geq$$

$$(S_E - S_N)\cdot\left[\left[\frac{(\beta N_{in\beta} - N_{in})}{n}\alpha + \frac{\beta}{\hat{n}}\sum_i^{N_b\beta}\alpha_\beta(i) - \frac{1}{n}\sum_i^{N_b}\alpha(i)\right]\right]$$

In Equation (7), the contrast is invariant as a function of voxel size when $\alpha_\beta(i)=\alpha(i)=1$. When the tumor region is much larger than the voxel size, both n and $\hat{n}/\beta$ are very large. The contrast variation is dominant by the first term $$\frac{(\beta N_{in\beta} - N_{in})}{n}\alpha.$$

For very large n, the voxel number which change from lesion-tissue boundary into inside and outside lesion region caused by reduced voxel size is ignorable, leading to very small $$\frac{(\beta N_{in\beta} - N_{in})}{n}.$$

Thus, the contrast caused by the first term can be approximated to be invariant. The result is in a good agreement with Equation (1). When the size of the lesion region is comparable to the voxel size, almost all voxels occur at the lesion-tissue boundary, the contrast variation is dominant by $$\left[\frac{\beta}{\hat{n}}\sum_{k}^{N_{b\beta}}\alpha_{\beta}(i) - \frac{1}{n}\sum_{k}^{N_{b}}\alpha(i)\right].$$

The higher spatial resolution or smaller voxel size provides a finer delineation of lesion-tissue boundary and then extracts some tissue cells from the lesion region which belong to the lesion region at lower spatial resolution. As a result, $$\sum_{k}^{N_{b\beta}}\alpha_{\beta}(i) > \sum_{k}^{N_{b}}\alpha(i).$$

That is, fraction of lesion cells increases for the lesion region with higher spatial resolution. Though a lesion region is given for a patient, the measured lesion region by contrast enhanced Mill is slightly variable with the spatial resolution. The difference between the lesion region and the measured lesion region will depend on the lesion size and image spatial resolution.

Figure 3A:
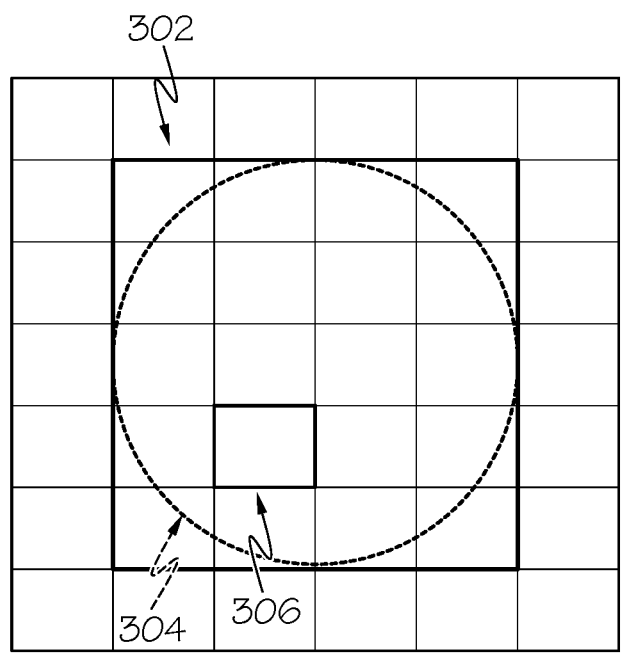
FIG. 3A illustrates a simplified image acquired with a relatively low spatial resolution according to one example in the present disclosure.
Figure 3B:
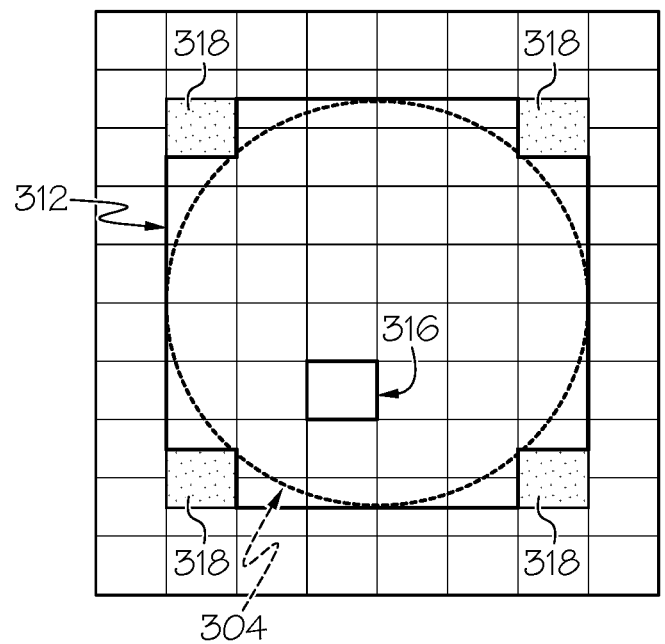
FIG. 3B illustrates a simplified image acquired with an increased spatial resolution according to one example in the present disclosure.

The difference will be apparent when the size of the lesion region is comparable to the size of a pixel or a voxel in an image FIGS. 3A and 3B show a simple explanation of principle of spatial resolution enhanced medical imaging, particularly for the object of interest with extrinsic partial volume effect. FIG. 3A illustrates a simplified image acquired with a relatively low spatial resolution and FIG. 3B illustrates a simplified image acquired with an increased spatial resolution. Solid lines 302, 312, dashed circles 304, 314, grid line 306, 316 respectively express measured lesion region, true lesion, and pixel size. In FIG. 3A, the measured lesion region 302 is a solid square. In FIG. 3B, with the increased spatial resolution, the measured lesion region 312 is a polygon. The measured lesion region 302 in FIG. 3A at low spatial resolution equals to the addition of the measured lesion region 312 in FIG. 3B and removed the shade grid parts 318. Thus, the ratio of a true lesion volume to a measured lesion volume increases as the spatial resolution increases because the shade grid parts 318 which are not part of the true lesion volume may be removed. That is, the partial volume effect at the lesion-tissue boundary can lead to an increased fraction of lesion for heterogenous objects with the increasing spatial resolution. As Equation (3) indicates, the increased fraction of lesion can enhance the lesion-tissue contrast. That is, increasing spatial resolution can enhance contrast for the objects with both extrinsic and intrinsic partial volume effect.

Example in MRI Cancer Imaging

Cancer is the second leading cause of deaths in the world. There were over 18 million new cancer cases and approximately 9 million people died from this disease globally. In the United States of America, almost two million new cases of cancer were diagnosed annually and over 600,000 people are estimated to die from the disease. The incidence of cancer is expected to rise because of population growth and aging. Early tumor detection is a critically important in controlling and management of cancer, which can lead to earlier interventions and optimal treatment choices. The early detection of brain tumor will improve quality of life, increase curability, and prolong patient survival. Therefore, minimally- and non-invasive methods for early detection of brain tumor are urgently needed.

Contrast enhanced magnetic resonance imaging (MRI) is a gold standard for brain tumor imaging because MRI is more sensitive than other imaging modalities, such as computer tomography (CT) and positron emission tomography (PET). Particularly, three-dimensional (3D) inversion-recovery gradient echo (IR-GRE) has been recommended by U.S. Food and Drug Administration (FDA) and National Cancer Institute (NCI) for brain tumor and brain metastasis imaging. However, the detection for small tumor lesion at the early stage till remain challenging.

The size of tissue cells is around ten micrometers, which is much less than a voxel size of MRI image (i.e. millimeter) which includes million tumor cells and normal tissue cells. The intrinsic partial volume effect in tumor lesion is one of the major factors limiting the detection sensitivity of tumor, particularly for small tumor with low imaging resolution. There is broad agreement that increased lesion-tissue contrast significantly improves detection confidence and accuracy in contrast enhanced MRI. For example, contrast enhanced MRI can detect 0.2 millimeter (mm) tumor lesions with the image spatial resolution of 0.1 mm in a recent preclinical animal study. In clinical practice, contrast enhanced MRI can confidently detect 5.0 mm tumor lesion with the image spatial resolution of more than 1.0 mm. The achievable spatial resolution is mainly limited by contrast-to-noise ratio and scan time in clinical practice. The improved lesion-tissue contrast has been reported by various methods.

Though 0.1 mmol/kg gadolinium-based contrast agents is a standard intravenous dose for contrast enhanced MRI, higher dose injection is known to be more effective in the detection of brain tumor. Recently, MRI signal changes in deep nuclei of the brain with repeated injection of gadolinium-based contrast agents confirm Gadolinium deposits. This evidence leads to the need to consider injection of potential risk of these agents. More of the injected dose of gadolinium in contrast enhanced MRI for improving detection of lesion potentially increase the risk of gadolinium-related toxicity, limiting the application of high dose gadolinium-based contrast agents.

MRI acquisition always includes a challenging trade-off among the achievable spatial resolution, temporal resolution, and volume coverage. A key advantage of the higher field strengths can provide the general signal-to-noise ratio (SNR) and contrast-to-noise ratio (CNR) gain compared with lower field strengths. The increased SNR translate, at least to a certain degree, into a higher spatial resolution. The increased CNR could increase the detection sensitivity of tumor lesions. Most recently, some studies exhibited that high field strength MRI was superior for the detection small lesion. But the cost-effectiveness of high field strength is an important issue in today's health care reform climate of cost containment.

Moreover, the transmit time of contrast agent strongly influences the detection sensitivity of contrast enhanced MRI. Previous studies proposed that the volume of brain tumor could increase significantly with the increased delayed time of contrast agent MRI acquisition. The delay time is limited by scan time for each patient and washout of contrast agent. For example, brain tumor imaging is limited to less than 60 minutes in clinical practices, and post-contrast images is acquired only during the final 20~30 minutes. Thus, the long delayed time is not available for most clinical practices.

Conventionally, the contrast between homogenous objects (such as gray matter and white matter) is invariant as a function of voxel size when the size of the homogeneous objects are more than the voxel size. However, it is not clear that this is available for the objects of interest with intrinsic partial volume effect, such as brain tumor. In the present invention, the relationship between spatial resolution and a tumor-tissue contrast is verified theoretically and experimentally. The increasing spatial resolution can enhance the tumor-tissue contrast and increase the detection sensitivity of tumor and recurrence during the treatment. The present method for increasing imaging contrasts provides a great potential in the early detection and the early treatment assessment of cancer.

Brain images of nine patients with brain tumors (4 pituitary tumors and 5 brain metastases) were obtained using the three-dimensional (3D) inversion recovery spoiled gradient recalled echo (IR-FSPGR) sequence with imaging parameters recommended by FDA and NCI: FOV 256×232 mm$^2$, echo time 2.8 milli-seconds, the inversion recovery time 450 milli-seconds flip angle 12°, the isotropic resolution of 1.2 mm, 1.0 mm, and 0.9 mm. Parallel acquisition was conducted in Asset mode with an acceleration factor of 2. In order to avoid the effect of contrast agent transmit time, the brain tumor images with different spatial resolutions were acquired in random acquisition order. Linear mixed models were used to compare the normalized contrast between isotropic resolutions by considering the correlation between measurements of different resolutions within each patient. Box plots were performed to illustrate the distribution of NCs for each isotropic resolution. All analyses were performed using SAS version 9.4. P-values less than 0.05 were considered statistically significant.

Figure 4C:
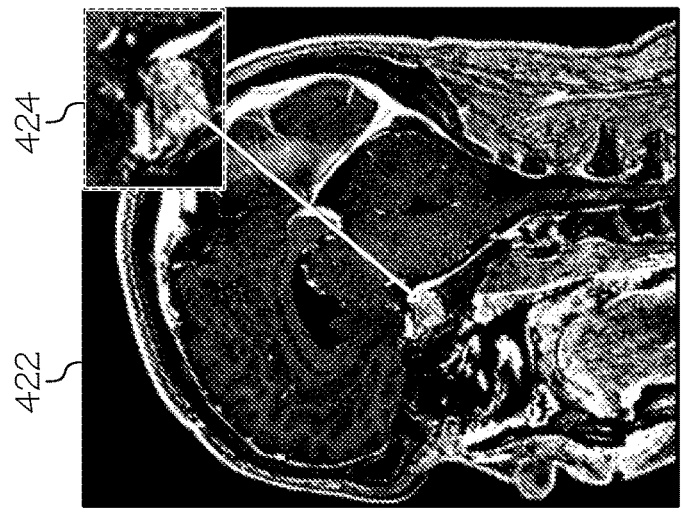
FIG. 4C shows an example of in vivo brain images of a patient with pituitary tumor acquired with a conventional T1-weighted protocol with an isotropic voxel size of 0.9 mm after the administration of 0.1 mmol/kg Gadavist.
Figure 4B:
FIG. 4B shows an example of in vivo brain images of a patient with pituitary tumor acquired with a conventional T1-weighted protocol with an isotropic voxel size of 1.0 mm after the administration of 0.1 mmol/kg Gadavist.
Figure 4A:
FIG. 4A shows an example of in vivo brain images of a patient with pituitary tumor acquired with a conventional T1-weighted protocol with an isotropic voxel size of 1.2 mm after the administration of 0.1 mmol/kg Gadavist.
Figure 4D:
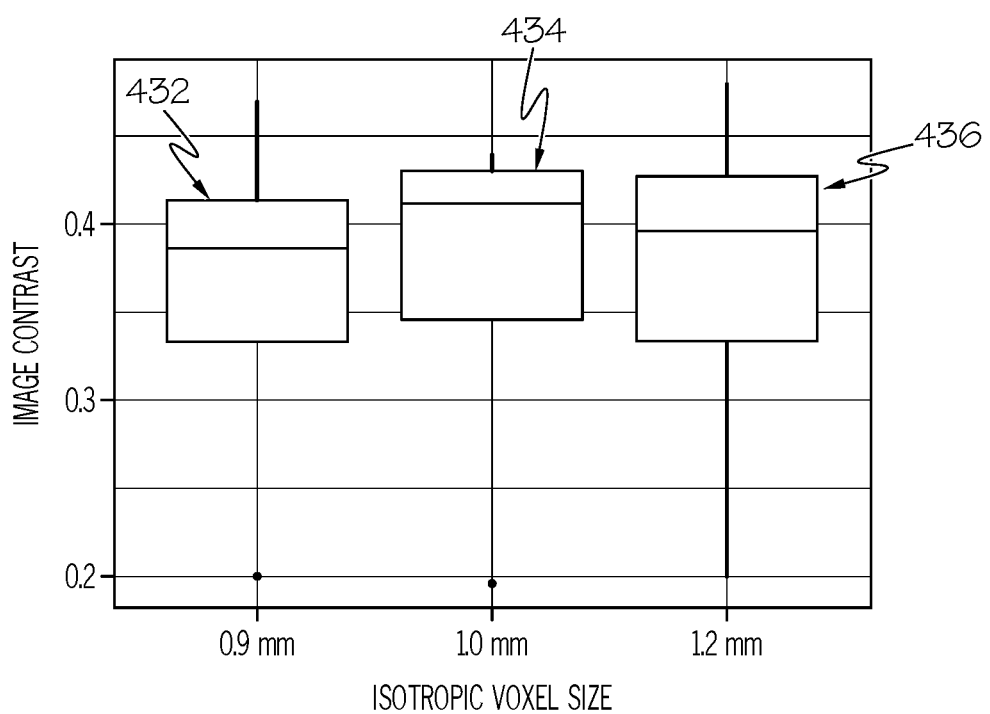
FIG. 4D shows quantitative estimation of the effect of different isotropic voxel sizes on tumor-tissue contrast of four patients with pituitary tumors in FIGS. 4A-4C.

FIGS. 4A-4C show in vivo brain images of a patient with pituitary tumor acquired with recommended IR-GRE sequence after the administration of 0.1 mmol/kg Gadavist. The image 402 is acquired with the lowest spatial resolution with an isotropic voxel size of 1.2 mm among the three images, the image 422 is acquired with the highest spatial resolution with an isotropic voxel size of 0.9 mm among the three images, and the image 412 is acquired with a pixel size of 1.0 mm. Visually, higher spatial resolution provides better definition of the pituitary tumor architecture and near-invariant tumor-tissue contrast according to one example in the present disclosure. With an in vivo comparison shown in FIG. 3, the increased spatial resolution leads to a more conspicuous description of lesions detail and internal structure, and the shaper tumor-tissue boundary. Quantitative analysis in FIG. 4D indicates that the tumor-brain tissue contrasts are 0.360±0.113, 0.365±0.114 and 0.367±0.120 for the isotropic voxel size of 1.2, 1.0 and 0.9 mm, respectively. There are no statistical differences on tumor-tissue contrast with the increasing spatial resolution when the tumor size is much larger than the spatial resolution. But, the signal intensity inhomogeneity increases apparently with the increasing spatial resolution.

Figure 5C:
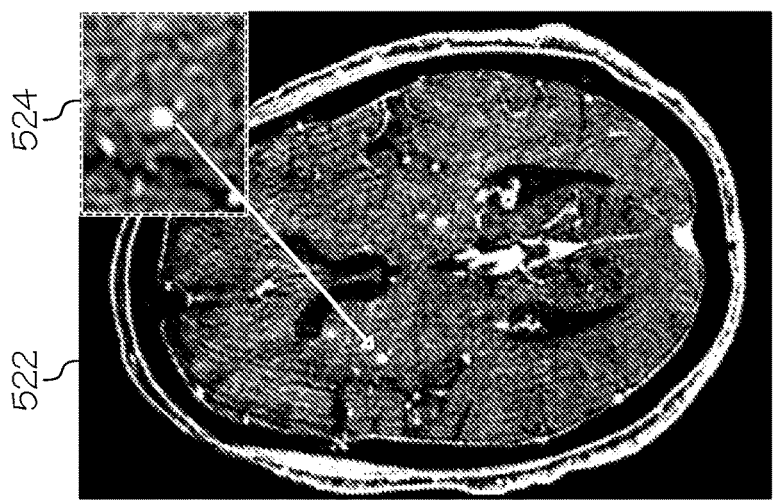
FIG. 5C shows an example of in vivo brain images of a patient with brain metastases acquired with recommended protocol with an isotropic voxel size of 0.9 mm after the administration of 0.1 mmol/kg Gadavist.
Figure 5B:
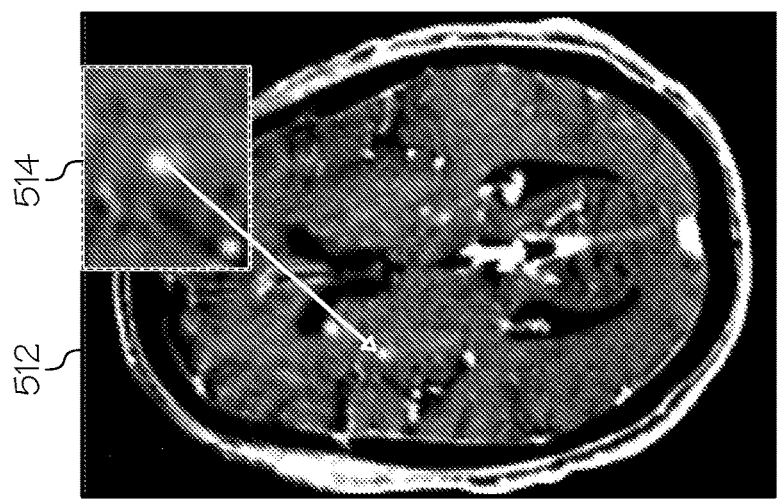
FIG. 5B shows an example of in vivo brain images of a patient with brain metastases acquired with recommended protocol with an isotropic voxel size of 1.0 mm after the administration of 0.1 mmol/kg Gadavist.
Figure 5A:
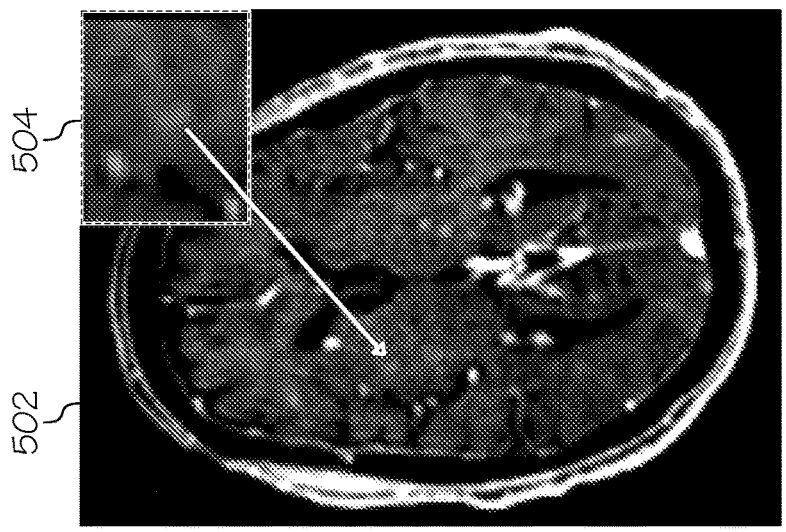
FIG. 5A shows an example of in vivo brain images of a patient with brain metastases acquired with recommended protocol with an isotropic voxel size of 1.2 mm after the administration of 0.1 mmol/kg Gadavist.
Figure 5D:
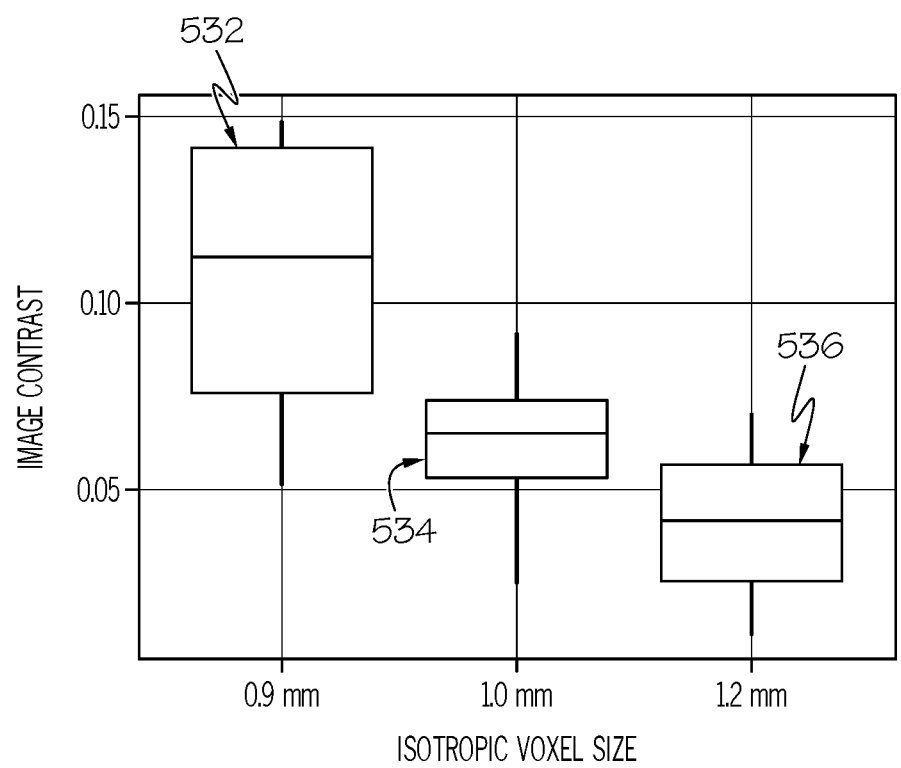
FIG. 5D shows quantitative estimation of the effect of different isotropic voxel sizes on normalized tumor-tissue contrast of four patients with brain metastases in FIGS. 5A-5C.

FIGS. 5A-5C show in vivo brain images of a patient with brain metastases acquired with recommended IR-GRE sequence after the administration of 0.1 mmol/kg Gadavist. The image 502 is acquired with the lowest spatial resolution with an isotropic voxel size of 1.2 mm among the three images, the image 522 is acquired with the highest spatial resolution with an isotropic voxel size of 0.9 mm among the three images, and the image 512 is acquired with the higher spatial resolution with an isotropic voxel size of 1.0 mm among the three images. Visually, higher spatial resolution provides higher tumor-tissue contrast according to one example in the present disclosure. With the increasing spatial resolution, more clear brain metastasis lesion is illustrated. Specifically, the brain metastasis lesion 524 is clearer than the brain metastasis lesion 514 which is clearer than the brain metastasis lesion 504. Quantitative analysis in FIG. 5D indicates that tumor-brain tissue contrasts 536, 534, 532 are 0.041±0.026, 0.061±0.028 and 0.110±0.046 for the isotropic voxel size of 1.2 mm, 1.0 mm and 0.9 mm, respectively. Additionally, the better sharpness is observed at the boundary of tumor-tissue. Even for the small sample size of 4 patients with brain metastases, the increased contrasts between the isotropic voxel size of 1.2 mm and 0.9 mm is statistically significant currently.

The visibility and detection sensitivity in medical image are mainly determined by the contrast of normal tissue-lesion. The endless goal of medical imaging techniques is to increase the contrast at the reasonable scan time. Generally, increasing spatial resolution will lead to a reduced contrast or invariant contrast for a targeted region which consists of voxels or pixels each including cells or molecules of a single type. Even at the boundary of region of interest, the contrast is still invariant when the pixel or voxel includes multiple components due to the partial volume effect. The size of cells or molecules is tens of micrometers, while the size of a pixel or a voxel is several millimeters. Each pixel or voxel includes million cells or molecules. In the field of medical imaging, the regions of interest always are assumed to be homogenous. That is, there exists a boundary among different tissues and lesions at the size of pixel or voxel levels. For example, a gray matter-white matter contrast in medical images are determined from signal difference between the regions of gray matters and the regions of white matters. Each of the regions of gray matters and the regions of white matters is homogeneous and there exists a gray matter-white matter boundary at the pixel or voxel size level. The gray matter-white matter contrast measured from radiological images is identical to a contrast between gray matter cells and white matter cells. However, it is not true for a heterogenous pixel or voxel in which a pixel or voxel consists of multiple components. For example, the pixel or voxel of tumor lesion includes both tumor cells and normal tissue cells. There is no tumor-tissue boundary at the pixel or voxel size level, and each pixel or voxel is heterogeneous. The contrast between tumor regions and tissue regions measured from radiological image should not be identical to the contrast between tumor cells and tissue cells. The present disclosure validates that the increased spatial resolution could increase the contrast in MRI when the size of the targeted region is comparable to the size of a voxel or pixel. For example, the increased spatial resolution could increase the contrast in MRI when the size of the targeted region is between the size of the voxel or pixel and several times of the size of the voxel or pixel. The obtained methods may extend to other image modalities. Increased spatial resolution can be realized by various methods, such as a higher field strength, increased scan time, and contrast agent.

As illustrated in FIGS. 4A-4D and 5A-5D, increasing spatial resolution does not have a statistically significant influence on the contrasts when the size of tumor is much larger than the size of the voxel or pixel of an image. However, increasing spatial resolution does have a significant influence when the size of tumor is comparable to the size of the voxel or pixel of the image. For example, sizes of pituitary tumors range between 8 mm and 18 mm and sizes of brain metastases range between 2 mm and 5 mm. Though increasing the spatial resolution reduces signal intensity for both enhanced tumor and non-enhanced tissues, reduced partial volume effect leads to an increased contrast with the increased spatial resolution when the tumor size is comparable to the voxel size of 1.0 mm. As a result, the increased spatial resolution enhances the contrast between normalized tumor and tissue, as shown in Equation (7). When the size of a tumor region is much larger than the voxel size, the number of voxels or pixels inside the tumor region is much greater than the number of voxels or pixels that are present at the boundary between tumor and tissue, such that the partial volume effect can be minimized or ignored.

The results obtained from both large and small size tumors are in good agreement with Equation (7). Therefore, the increased spatial resolution can enhance tumor-tissue contrast when the tumor size is comparable to the spatial resolution.

There is broad agreement that the lesion-tissue contrast closely associates with visibility and detection sensitivity of lesion. Conventionally, the MRI image contrast between homogenous objects (such as gray matter and white matter) is invariant as a function of spatial resolution. That is, the spatial resolution and lesion-tissue contrast may individually contribution to the detection of small lesions for homogeneous objects with extrinsic partial volume effect. In the present invention, we first reveal the correlation between tumor-tissue contrast and spatial resolution for the objects of interest with intrinsic partial volume effect, such as tumor. The present method has the following advantages over conventional methods: First, the present method has a good generality. Though the present method is only validated for 3D IR-GRE brain cancer imaging, the present method can be also extended to other MRI modalities, such as dynamic contrast enhanced MRI, dynamic susceptibility contrast MRI, and diffusion MRI. Second, the present method can be implemented for medical imaging which the pixel or voxel consist of a heterogeneous architecture system. For example, the system can consist of both healthy tissue cells and tumor cells. Additionally, the system can also consist of tumor with or without contrast enhancements. Third, the increased tumor-tissue contrast by the increased spatial resolution in the present can be traded to reduce the dose of contrast agent, leading to the reduced cost and potential risk without any penalty of image quality in clinical practices. For example, contrast enhanced MRI at 3.0 T with half the dose of contrast agent can provide an equivalent performance of lesion conspicuity at 1.5 T with the full dose of contrast agent.

There exist major two innovations in the present invention. First, the present invention devises the concept of intrinsic partial volume effect which is totally different from conventional partial volume effect (i.e., extrinsic partial volume effect) at the boundary of different tissues or regions. This is a popular biomedical phenomenon. Second, the present invention theoretically and experimentally demonstrates that the increasing spatial resolution can increase pathophysiological contrast. This provides a low cost and effective method for improving visibility and detection of small pathophysiological changes. It holds a great potential in the early detection of various diseases and early assessment of therapy response. Finally, the increased contrast by the increased spatial resolution can further improve achievable spatial resolution when the voxel size under the increased spatial resolution is comparable to the size of a region of interest or a lesion with a fixed size. With the spatial resolution being further increased, the size of the region of interest or the lesion may become much larger than the voxel size under the further increased spatial resolution.

In that case, further increasing the spatial resolution do not further increase the contrast as illustrated in FIGS. 4A-4C. The present invention also indicates complex relationship between the voxel size under the achievable spatial resolution and the size of the region of interest detectable. This is very important to detect the small or subtle pathophysiological changes.

The present technique and method can extend to any medical imaging modalities, including X-ray, computed tomography (CT), ultrasound, but not limited to, magnetic resonance imaging (MRI), magnetic resonance spectroscopy (MRS), magnetic resonance spectroscopy imaging (MRSI), positron emission tomography (PET), near-infrared (NIR) fluorescence imaging, nuclear medicine imaging, and their variations. Additionally, a region of interest with intrinsic partial volume effect can indicate that a voxel or a pixel includes both healthy tissue cells and pathological tissue cells. The contrast for heterogeneous region of interest depends on not only the voxel size or the pixel size, but also the fraction of pathological tissue cells as shown in Equation (4). In Equation (4), the contrast is proportional to the fraction of the pathological tissue cells. Thus, when the size of a voxel or a pixel decreases as spatial resolution increases, the fraction of pathological tissue cells a may increase as Equation (7) when the lesion size is comparable to the voxel or pixel size. Thus, contrary to the conventional notion that contrast is invariant for homogeneous region of interest, the present disclosure obtains images with greater contrast for regions having a mixture of healthy tissue cells and pathological tissue cells by increase spatial resolution.

The design of medical imaging involves several tradeoffs, especially between spatial resolution, sensitivity, and temporal resolution. Spatial resolution remains one major limitation for medical imaging. For example, the voxel size of PET imaging is more than 2.0 mm in clinical practices. Conventionally, the size of a voxel or pixel of CT imaging is often more than 1.0 mm in clinical practices because of low-contrast detectability and dose limitation. In contrast, the present method leverages these high spatial resolution techniques to perform accurate detection and characterization in diagnosis and treatment assessment for heterogeneous regions of interest, such as cancer and neurodegenerative diseases. The accurate detection and characterization of lesion will benefit for early detection and early treatment assessment of various diseases.

The increase of the spatial resolution for an image may be limited by the signal-to-noise ratio of the image which decreases when the spatial resolution increases. Various techniques, such as better coil design, high field strength and optimization of sequence, may improve the signal-to-noise ratio and lead to increased spatial resolution. For example, application of hybrid k-space trajectory and variable flip angle may improve the signal-to-noise ratio. With the developments of these techniques, the signal-to-noise of medical imaging can be greatly improved. One can apply the proposed technique and method in the diagnosis and treatment assessment.

The present disclosure describes 3D IR-GRE contrast enhanced MRI imaging to demonstrate and validate that the increased spatial resolution can increase tumor-tissue contrast when the tumor size is comparable to the voxel or pixel size of acquired images. Other MRI sequences are also common for cancer imaging, such as turbo spin echo sequences with variable flip angles, diffusion MRI, echo planar imaging with or without magnetization preparation.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

The invention claimed is:

1. A method for spatial resolution enhanced imaging, the method comprising:
   determining a target region of a subject being imaged;
   estimating an achievable spatial resolution;
   selecting an increased spatial resolution that is greater than a predetermined spatial resolution and equal to or less than the achievable spatial resolution; and
   acquiring image data of the target region with the increased spatial resolution, wherein a voxel or a pixel of the image data corresponding to a region of interest in the target region includes intrinsic partial volume effect and another voxel or pixel of the image data corresponding to a boundary of the region of interest in the target region includes extrinsic partial volume effect,
   wherein a contrast between the region of interest and other tissue region in the image data acquired with the increased spatial resolution is greater than a contrast between the region of interest and other tissue region in the image data acquired with the predetermined spatial resolution due to the intrinsic partial volume effect.

2. The method of claim 1, wherein the voxel or pixel of the image data corresponding to the region of interest further comprises cells and molecules with the different pathological or physiological features that are characterized by radiomic features derived from the radiological images.

3. The method of claim 1, further comprising:
   administering contrast agent,
   wherein the intrinsic partial volume effect consists of a cell with contrast agent leakage and a cell without contrast agent leakage.

4. The method of claim 1, wherein the intrinsic partial volume effect consists of a lesion cell and a non-lesion cell.

5. The method of claim 1, wherein the image data is acquired with functional imaging; and
   the intrinsic partial volume effect consists of excited neurons and non-excited neurons.

6. The method of claim 1, wherein the image data of the subject is received from one of, X-ray, computed tomography (CT), ultrasound, magnetic resonance imaging (MRI), magnetic resonance spectroscopy (MRS), magnetic resonance spectroscopy imaging (MRSI), positron emission tomography (PET), near-infrared (NIR) fluorescence imaging, nuclear medicine imaging, and their variations.

7. The method of claim 1, wherein the increased spatial resolution is greater than a half of the achievable spatial resolution.

8. The method of claim 1, wherein the increased spatial resolution is between a half of the achievable spatial resolution and two thirds of the achievable spatial resolution.

9. The method of claim 1, wherein the increased spatial resolution is between two thirds of the achievable spatial resolution and the achievable spatial resolution.

10. The method of claim 7, wherein the achievable spatial resolution is determined by various factors including imaging modalities, hardware, imaging parameters, acquisition time, and image reconstruction.

11. The method of claim 7, further comprising implementing one of lesion detection, disease diagnosis, treatment planning and treatment assessment based on the acquired image data.

12. The method of claim 1, wherein the predetermined spatial resolution is a spatial resolution used in clinical or research practice.

13. A system for contrast enhancement, the system comprising:
   a processor configured to:
      determine a target region of a subject being imaged;
      estimate an achievable spatial resolution; and
      select an increased spatial resolution that is greater than a predetermined spatial resolution and equal to or less than the achievable spatial resolution; and
   a receiver configured to acquire image data of the target region with the increased spatial resolution, wherein a voxel or a pixel of the image data corresponding to a region of interest in the target region includes intrinsic partial volume effect and another voxel or pixel of the image data corresponding to a boundary of the region of interest in the target region includes extrinsic partial volume effect,
   wherein a contrast between the region of interest and other tissue region in the image data acquired with the increased spatial resolution is greater than a contrast between the region of interest and other tissue region in image data acquired with the predetermined spatial resolution due to the intrinsic partial volume effect.

14. The system of claim 13, wherein the voxel or pixel of the image data corresponding to the region of interest further comprises cells and molecules with the different pathological or physiological features that are characterized by radiomic features derived from the radiological images.

15. The system of claim 13, wherein the intrinsic partial volume effect includes a cell with contrast agent leakage and a cell without contrast agent leakage.

16. The system of claim 13, wherein the image data is acquired with functional imaging; and
   the intrinsic partial volume effect include excited neurons and non-excited neurons.

17. The system of claim 13, wherein the increased spatial resolution is greater than a half of the achievable spatial resolution.

18. The system of claim 13, wherein the increased spatial resolution is between a half of the achievable spatial resolution and two thirds of the achievable spatial resolution.

19. The system of claim 13, wherein the increased spatial resolution is between two thirds of the achievable spatial resolution and the achievable spatial resolution.

20. The system of claim 13, wherein the controller reduces a dose of a contrast agent to be applied to the subject when image data of the subject is acquired with the increased spatial resolution to be less than a dose of the contrast agent to be applied to the subject when image data of the subject is acquired with the predetermined spatial resolution.

* * * * *